US012573138B2

(12) United States Patent
Saiga et al.

(10) Patent No.: US 12,573,138 B2
(45) Date of Patent: \*Mar. 10, 2026

(54) ENDOSCOPIC EXAMINATION SUPPORT APPARATUS, ENDOSCOPIC EXAMINATION SUPPORT METHOD, AND RECORDING MEDIUM

(71) Applicant: NEC Corporation, Tokyo (JP)

(72) Inventors: Hiroyasu Saiga, Tokyo (JP); Tatsu Kimura, Tokyo (JP)

(73) Assignee: NEC CORPORATION, Tokyo (JP)

( \* ) Notice: Subject to any disclaimer, the term of this patent is extended or adjusted under 35 U.S.C. 154(b) by 40 days.

This patent is subject to a terminal disclaimer.

(21) Appl. No.: 18/396,990

(22) Filed: Dec. 27, 2023

(65) Prior Publication Data

US 2024/0127531 A1 Apr. 18, 2024

Related U.S. Application Data

(63) Continuation of application No. 18/559,088, filed as application No. PCT/JP2023/028002 on Jul. 31, 2023.

(51) Int. Cl.
*G06T 17/00* (2006.01)
*A61B 1/00* (2006.01)
(Continued)

(52) U.S. Cl.
CPC ........ *G06T 17/00* (2013.01); *A61B 1/000094* (2022.02); *A61B 1/000096* (2022.02); (Continued)

(58) Field of Classification Search
CPC ......... G06T 17/00; G06T 7/0012; G06T 7/55; G06T 7/74; G06T 2200/08; (Continued)

(56) References Cited

U.S. PATENT DOCUMENTS 7,706,600 B2 \* 4/2010 Kreeger ................... G06T 7/12
382/128
2007/0003131 A1 1/2007 Kaufman
(Continued)

FOREIGN PATENT DOCUMENTS

JP 2007-282857 A 11/2007
JP 2017-225700 A 12/2017
(Continued)

OTHER PUBLICATIONS

International Search Report for PCT Application No. PCT/JP2023/028002, mailed on Oct. 10, 2023.
(Continued)

*Primary Examiner* — Daniel F Hajnik
(74) *Attorney, Agent, or Firm* — Sughrue Mion, PLLC

(57) ABSTRACT

In the endoscopic examination support apparatus, the three-dimensional model generation means generates a three-dimensional model of a luminal organ in which an endoscope camera is placed, based on endoscopic images obtained by imaging an interior of the luminal organ with the endoscope camera. The unobserved area detection means detects an area estimated not to be observed by the endoscope camera, as an unobserved area, based on the three-dimensional model. The display image generation means generates a display image including at least one of information indicating a position of the unobserved area in the endoscopic image, and information indicating a direction of the unobserved area outside the endoscopic image. The endoscopic examination support apparatus may be used to support user's decision making.

11 Claims, 8 Drawing Sheets

100: ENDOSCOPIC EXAMINATION SYSTEM

(51) Int. Cl.

| | | |
|---|---|---|
| *G06T 7/00* | (2017.01) | |
| *G06T 7/55* | (2017.01) | |
| *G06T 7/73* | (2017.01) | |
| *G16H 50/50* | (2018.01) | |

(52) U.S. Cl.
CPC ........ *A61B 1/0005* (2013.01); *A61B 1/00194* (2022.02); *G06T 7/0012* (2013.01); *G06T 7/55* (2017.01); *G06T 7/74* (2017.01); *G16H 50/50* (2018.01); *G06T 2200/08* (2013.01); *G06T 2207/10016* (2013.01); *G06T 2207/10068* (2013.01); *G06T 2207/20081* (2013.01); *G06T 2207/30096* (2013.01); *G06T 2207/30244* (2013.01); *G06T 2210/41* (2013.01)

(58) Field of Classification Search
CPC . G06T 2207/10016; G06T 2207/10068; G06T 2207/20081; G06T 2207/30096; G06T 2207/30244; G06T 2210/41; G06T 7/246; G06T 2200/24; G06T 2207/20084; G06T 2207/30092; A61B 1/000094; A61B 1/000096; A61B 1/0005; A61B 1/00194; A61B 1/00055; A61B 2034/105; A61B 2090/367; G16H 50/50; G16H 20/40; G06V 2201/03
See application file for complete search history.

(56) References Cited

U.S. PATENT DOCUMENTS

| | | | |
|---|---|---|---|
| 2009/0041320 | A1 | 2/2009 | Tanaka |
| 2011/0187707 | A1* | 8/2011 | Kaufman ............. A61B 1/0005 |
| | | | 345/419 |
| 2017/0112578 | A1* | 4/2017 | Ikuma ...................... A61B 1/05 |
| 2018/0368920 | A1* | 12/2018 | Ummalaneni ........... A61B 5/06 |
| 2019/0080454 | A1* | 3/2019 | Hameed ............. A61B 1/00177 |
| 2020/0297444 | A1* | 9/2020 | Camarillo ............. G16H 30/40 |
| 2021/0106208 | A1 | 4/2021 | Iwaki |
| 2021/0145523 | A1 | 5/2021 | Xing et al. |
| 2022/0398771 | A1 | 12/2022 | Hane |
| 2022/0400931 | A1 | 12/2022 | Hane |
| 2022/0409030 | A1 | 12/2022 | Hane |
| 2022/0414880 | A1 | 12/2022 | Inoue et al. |
| 2023/0165433 | A1 | 6/2023 | Demura |
| 2023/0194850 | A1 | 6/2023 | Shino et al. |
| 2024/0135642 | A1 | 4/2024 | Saiga et al. |
| 2024/0156325 | A1 | 5/2024 | Levine et al. |

FOREIGN PATENT DOCUMENTS

| | | | |
|---|---|---|---|
| WO | 2016/009701 | A1 | 1/2016 |
| WO | 2019/244255 | A1 | 12/2019 |
| WO | 2021/166103 | A1 | 8/2021 |
| WO | 2021/171464 | A1 | 9/2021 |
| WO | 2021/171465 | A1 | 9/2021 |
| WO | 2021/176664 | A1 | 9/2021 |
| WO | 2021/234907 | A1 | 11/2021 |
| WO | 2022/014077 | A1 | 1/2022 |

OTHER PUBLICATIONS

US Office Action for U.S. Appl. No. 18/559,088, mailed on Oct. 9, 2025.
US Office Action for U.S. Appl. No. 18/396,888, mailed on Dec. 18, 2025.
US Office Action for U.S. Appl. No. 18/559,088, mailed on Feb. 5, 2026.

* cited by examiner

100 : ENDOSCOPIC EXAMINATION SYSTEM

ENDOSCOPIC EXAMINATION SUPPORT APPARATUS, ENDOSCOPIC EXAMINATION SUPPORT METHOD, AND RECORDING MEDIUM

This application is a Continuation of U.S. application Ser. No. 18/559,088 filed on Nov. 6, 2023, which is a National Stage Entry of PCT/JP2023/028002 filed on Jul. 31, 2023, which claims priority from PCT International Application PCT/JP2022/029426 filed on Aug. 1, 2022, the contents of all of which are incorporated herein by reference, in their entirety.

TECHNICAL FIELD

The present disclosure relates to techniques available in presenting information to support an endoscopic examination.

BACKGROUND ART

Conventionally, there are known techniques for presenting information to support an endoscopic examination.

Specifically, for example, Patent Document 1 discloses a viewpoint in which, based on an image obtained by imaging an interior of a large intestine, information indicating a portion which can be analyzed and a portion which cannot be analyzed in the large intestine are displayed in a condition associated with a structure of the large intestine. Further, for example, Patent Document 1 discloses a viewpoint of determining a portion which is located in the field of view of the image sensor, which is visible on the captured image, and whose imaging condition is good, as the portion that can be analyzed, and determines the other portion as the portion that cannot be analyzed. Further, for example, Patent Document 1 discloses a viewpoint of detecting a portion having a high probability of being finally missed, out of the aforementioned portions that cannot be analyzed, as a missed portion.

PRECEDING TECHNICAL REFERENCES

Patent Document

Patent Document 1: International Publication WO2021/171464

SUMMARY

Problem to be Solved

However, according to Patent Document 1, there is no disclosure of a specific technique for presenting information indicating whether or not an observation is actually performed in the area while updating the information in real time, during an endoscopic examination.

Therefore, according to the technique disclosed in Patent Document 1, for example, during the endoscopic examination, the number or frequency of the operation to observe the area where the observation is not performed is increased, and therefore there is a possibility that an excessive burden is imposed on the operator performing the endoscopic examination.

It is an object of the present disclosure to provide an endoscopic examination support apparatus that can reduce the burden imposed on an operator performing the endoscopic examination.

Means for Solving the Problem

According to an example aspect of the present invention, there is provided an endoscopic examination support apparatus comprising:

a three-dimensional model generation means configured to generate a three-dimensional model of a luminal organ in which an endoscope camera is placed, based on endoscopic images obtained by imaging an interior of the luminal organ with the endoscope camera;

an unobserved area detection means configured to detect an area estimated not to be observed by the endoscope camera, as an unobserved area, based on the three-dimensional model; and a display image generation means configured to generate a display image including at least one of information indicating a position of the unobserved area in the endoscopic image, and information indicating a direction of the unobserved area outside the endoscopic image.

According to another example aspect of the present invention, there is provided an endoscopic examination support method comprising:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including at least one of information indicating a position of the unobserved area in the endoscopic image, and information indicating a direction of the unobserved area outside the endoscopic image.

According to still another example aspect of the present invention, there is provided a recording medium storing a program, the program causing a computer to execute:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including at least one of information indicating a position of the unobserved area in the endoscopic image, and information indicating a direction of the unobserved area outside the endoscopic image.

Effect

According to the present disclosure, the burden imposed on the operator performing the endoscopic examination can be reduced.

EXAMPLE EMBODIMENTS

Preferred example embodiments of the present invention will be described with reference to the accompanying drawings.

First Example Embodiment

[System Configuration]

Figure 1:
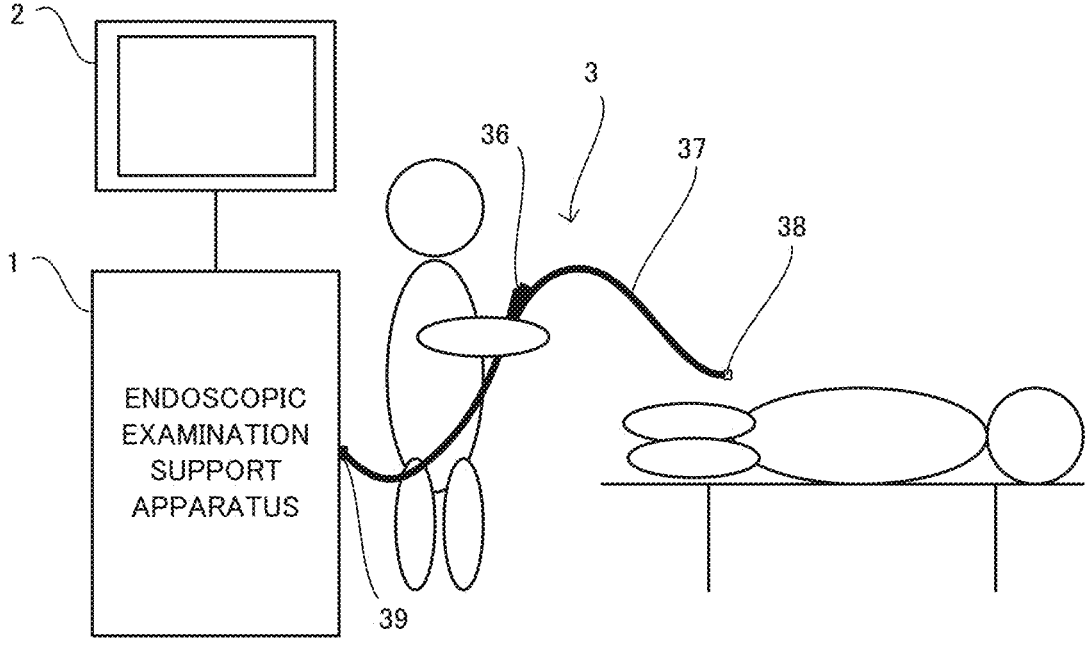
FIG. 1 is a diagram showing a schematic configuration of an endoscopic examination system according to a first example embodiment.

FIG. 1 is a diagram showing a schematic configuration of an endoscopic examination system according to a first example embodiment. The endoscopic examination system 100 includes an endoscopic examination support apparatus 1, a display device 2, and an endoscope 3 connected to the endoscopic examination support apparatus 1, as shown in FIG. 1.

The endoscopic examination support apparatus 1 acquires a video including time-series images obtained by imaging a subject (hereinafter, also referred to as "endoscopic video Ic") from the endoscope 3 during the endoscopic examination, and displays a display image for confirmation by an operator such as a doctor performing the endoscopic examination on the display device 2. Specifically, the endoscopic examination support apparatus 1 acquires a video of the interior of the large intestine obtained during the endoscopic examination from the endoscope 3 as an endoscopic video Ic. The endoscopic examination support apparatus 1 estimates the distance (hereinafter, also referred to as "depth") between the surface of the large intestine, which is a luminal organ, and the endoscope camera provided at the tip portion 38 of the endoscope 3, and the relative posture change of the endoscope camera, based on the images (hereinafter, also referred to as "endoscopic images") extracted from the endoscopic video Ic. Then, the endoscopic examination support apparatus 1 generates a three-dimensional model according to the structure of the large intestine by performing three-dimensional restoration based on the depth and the relative posture change of the endoscope camera. Also, the endoscopic examination support apparatus 1 detects, based on the endoscopic images, the observation difficult area which is an area estimated to be difficult to observe in the endoscopic examination. Also, the endoscopic examination support apparatus 1 detects a lesion candidate area, which is an area estimated as a lesion candidate, based on the endoscopic images. Also, the endoscopic examination support apparatus 1 detects the missing area which is missing in the three-dimensional model because the three-dimensional restoration is not performed or insufficient. Also, the endoscopic examination support apparatus 1 detects at least one of the observation difficult area and the missing area in the three-dimensional model as the unobserved area. Also, the endoscopic examination support apparatus 1 generates a display image based on the endoscopic image corresponding to the current position of the endoscope camera and the detection result of the unobserved area, and outputs the generated display image to the display device 2.

Incidentally, the observation difficult area may include, for example, an area that is difficult to visually recognize due to insufficient brightness, an area that is difficult to visually recognize due to the level of blurring, and an area where the state of the mucosal surface cannot be visually recognize due to the presence of the residue. The missing area may include, for example, an area hidden by a shield in the large intestine such as folds, and an area where imaging by the endoscope camera is not performed continuously for a predetermined time or more. The predetermined time described above may be set to 1 second, for example.

The display device 2 includes, for example, a liquid crystal monitor or the like. Further, the display device 2 displays the display image or the like outputted from the endoscopic examination support apparatus 1.

The endoscope 3 mainly includes an operation unit 36 for an operator to input instructions such as air supply, water supply, angle adjustment, and an image-capturing, a shaft 37 having flexibility and inserted into an organ of a subject to be examined, a tip portion 38 with a built-in endoscope camera such as an ultra-compact imaging element, and a connection unit 39 for connection with the endoscopic examination support apparatus 1.

[Hardware Configuration]

Figure 2:
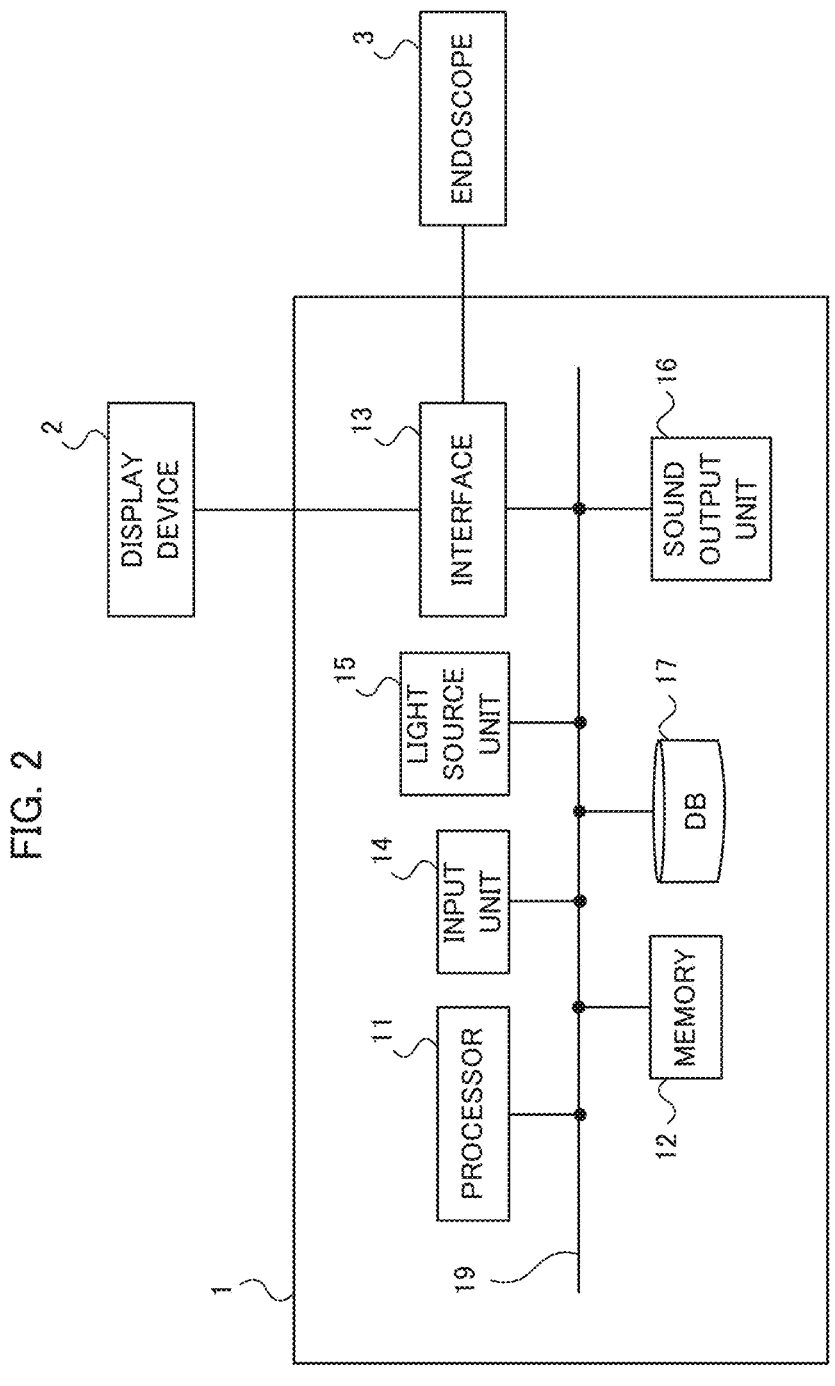
FIG. 2 is a block diagram showing a hardware configuration of an endoscopic examination support apparatus according to the first example embodiment.

FIG. 2 is a block diagram illustrating a hardware configuration of an endoscopic examination support apparatus according to the first example embodiment. The endoscopic examination support apparatus 1 mainly includes a processor 11, a memory 12, an interface 13, an input unit 14, a light source unit 15, a sound output unit 16, and a database (hereinafter, referred to as "DB") 17. Each of these elements is connected via a data bus 19.

The processor 11 executes predetermined processing by executing a program stored in the memory 12. The processor 11 is a processor such as a CPU (Central Processing Unit), a GPU (Graphics Processing Unit), and a TPU (Tensor Processing Unit). The processor 11 may be configured by multiple processors. The processor 11 is an example of a computer. The processor 11 also performs processing related to the generation of a display image based on the endoscopic images included in the endoscopic video Ic.

The memory 12 may include various volatile memories used as working memories, such as RAM (Random Access Memory) and ROM (Read Only Memory), and non-volatile memories for storing information needed for processing by the endoscopic examination support apparatus 1. Incidentally, the memory 12 may include an external storage device such as a hard disk connected to or incorporated in the endoscopic examination support apparatus 1, and may include a storage medium such as a removable flash memory or a disk medium. In the memory 12, a program for the endoscopic examination support apparatus 1 to execute each process in the present example embodiment is stored.

The memory 12 also temporarily stores a series of endoscopic videos Ic captured by the endoscope 3 during the endoscopic examination, based on the control of the processor 11.

The interface 13 performs an interface operation between the endoscopic examination support apparatus 1 and an external device. For example, the interface 13 supplies a display image generated by the processor 11 to the display device 2. The interface 13 also supplies the illumination light generated by the light source unit 15 to the endoscope 3. The interface 13 also provides an electrical signal indicating the endoscopic video Ic supplied from the endoscope 3 to the processor 11. The interface 13 also provides the endoscopic images extracted from the endoscopic video Ic to the processor 11. The interface 13 may be a communication interface such as a network adapter for wired or wireless communication with an external device, or may be a hardware interface compliant with a USB (Universal Serial Bus), a SATA (Serial AT Attachment), etc.

The input unit 14 generates an input signal based on the operation by the operator. The input unit 14 is, for example, a button, a touch panel, a remote controller, a voice input device, or the like. The light source unit 15 generates light to be supplied to the tip portion 38 of the endoscope 3. The light source unit 15 may also incorporate a pump or the like for delivering water or air to the endoscope 3. The sound output unit 16 outputs the sound based on the control of the processor 11.

The DB 17 stores the endoscopic videos acquired by the past endoscopic examination of the subject. The DB 17 may include an external storage device such as a hard disk connected to or incorporated in the endoscopic examination support apparatus 1, and may include a storage medium such as a removable flash memory. Instead of providing the DB 17 in the endoscopic examination system 100, the DB 17 may be provided in an external server or the like to acquire relevant information from the server through communication.

Incidentally, the endoscopic examination support apparatus 1 may be provided with a sensor capable of measuring the rotation and translation of the endoscope camera, such as a magnetic sensor.

[Functional Configuration]

Figure 3:
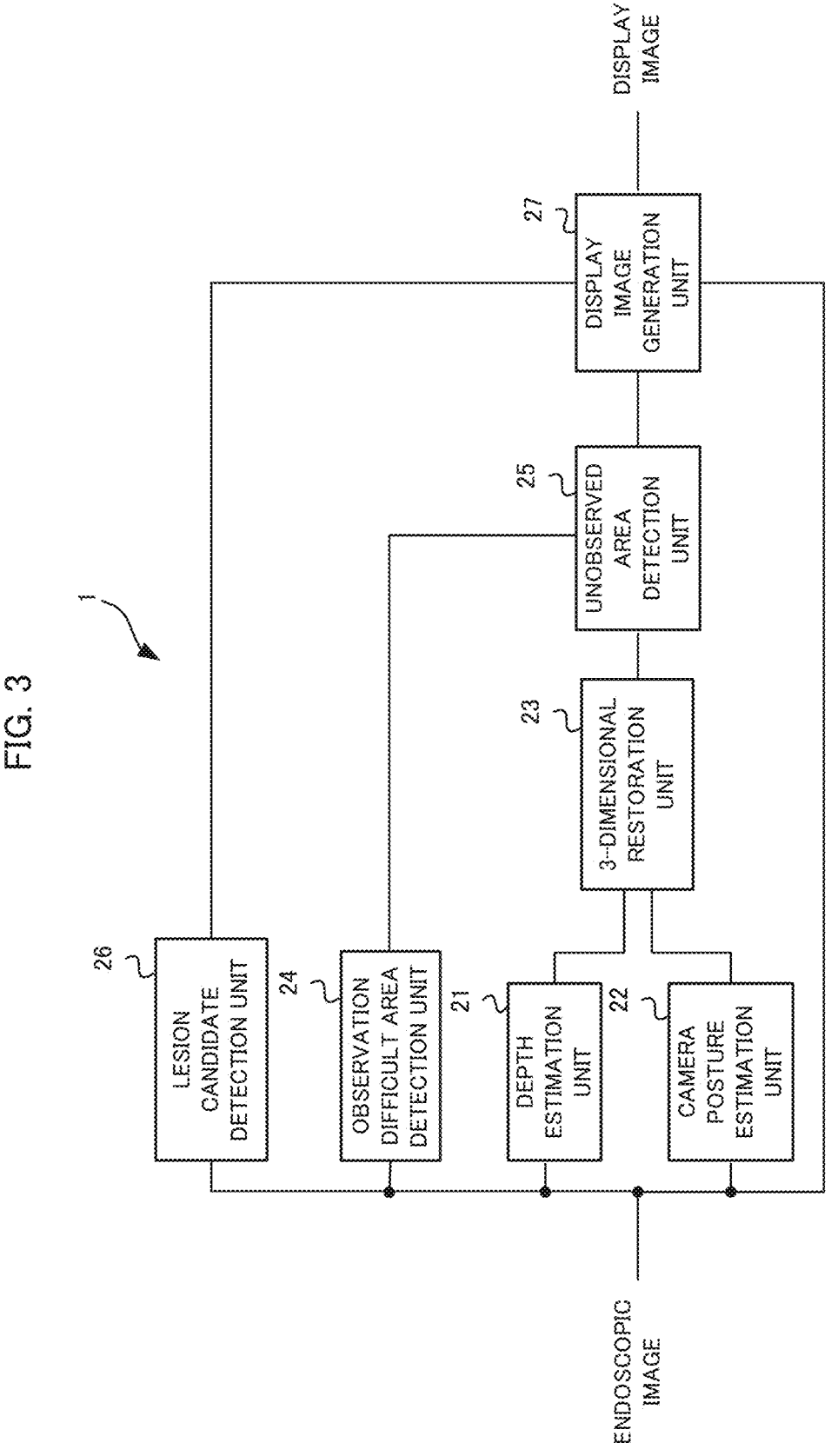
FIG. 3 is a block diagram showing a functional configuration of the endoscopic examination support apparatus according to the first example embodiment.

FIG. 3 is a block diagram illustrating a functional configuration of the endoscopic examination support apparatus according to the first example embodiment. The endoscopic examination support apparatus 1 functionally includes a depth estimation unit 21, a camera posture estimation unit 22, a three-dimensional restoration unit 23, an observation difficult area detection unit 24, an unobserved area detection unit 25, a lesion candidate detection unit 26, and a display image generation unit 27.

The depth estimation unit 21 performs processing for estimating the depth from the endoscopic images using a learned image recognition model or the like. That is, the depth estimation unit 21 has a function as a distance estimation means and estimates the distance between the surface of the luminal organ and the endoscope camera placed in the luminal organ, based on the endoscopic images obtained by imaging the interior of the luminal organ by the endoscope camera. The depth estimation unit 21 outputs the depth estimated by the above-described processing to the three-dimensional restoration unit 23.

The camera posture estimation unit 22 uses two endoscopic images successive in time to perform processing for estimating the rotation and translation of the endoscope camera from the imaging point of the first endoscopic image to the imaging point of the second endoscopic image (i.e., the relative posture change of the endoscope camera, hereinafter simply referred to as "camera posture change"). The camera posture estimation unit 22 performs processing for estimating the camera posture change using a learned image recognition model, for example. That is, the camera posture estimation unit 22 has a function as the posture change estimation means and estimates the relative posture change of the endoscope camera based on the endoscopic images obtained by imaging the interior of the luminal organ by the endoscope camera. The camera posture estimation unit 22 outputs the camera posture change estimated by the above-described processing to the three-dimensional restoration unit 23. The camera posture estimation unit 22 may estimate the camera posture change by using the measurement data acquired from the magnetic sensor or the like.

Here, the image recognition models used in the depth estimation unit 21 and the camera posture estimation unit 22 are machine learning models that are learned, in advance, to estimate the depth and the camera posture change from the endoscopic images. Hereafter, these models are also referred to as "the depth estimation model" and "the camera posture estimation model". The depth estimation model and the camera posture estimation model can be generated by so-called supervised learning.

For the learning of the depth estimation model, for example, teacher data in which the depth is given to an endoscopic image as a correct answer label is used. The endoscopic images and depths used for the learning are collected, in advance, from the endoscope camera and the ToF (Time of Flight) sensor installed in the endoscope. That is, a pair of an RGB image obtained by the endoscope camera and a depth obtained by the ToF sensor is created as teaching data, and learning is performed using the created teaching data.

In addition, for the learning of the camera posture estimation model, for example, teacher data in which the posture change of the endoscope camera is given to the endoscopic images as a correct answer label is used. In this case, the posture change of the endoscope camera can be obtained by using a sensor capable of detecting rotation and translation, such as a magnetic sensor. That is, a pair of an RGB image obtained by then endoscope camera and a posture change of the endoscope camera obtained by the sensor is created as teaching data, and learning is performed using the teaching data.

The teacher data used to learn the depth estimation model and the camera posture estimation model may be created from a simulation video of the endoscope using CG (computer graphics). By doing this, a large amount of teacher data can be created at high speed. The machine learning device uses the teacher data to learn the relationship of the endoscopic images to the depth and the camera posture change, thereby generating the depth estimation model and the camera posture estimation model.

The depth estimation model and the camera posture estimation model may be generated by self-supervised learning. For example, in self-supervised learning, motion parallax is utilized to create teacher data. Specifically, in self-supervised learning, a pair of images of an endoscopic image $I_i$ and an endoscopic image $I_j$, a Depth CNN (Convolutional Neural Network) for estimating a depth from the endoscopic image $I_i$ and a Pose CNN for estimating a relative posture from the endoscopic image $I_i$ and the endoscopic image $I_j$ are prepared. Then, the endoscopic image $I_j$ is reconstructed from the endoscopic image $I_i$ based on the depth estimated by the Depth CNN and the relative posture estimated by the Pose CNN (this is called "the endoscopic image $I_{i \to j}$"). Then, learning of the model is performed using the difference between the reconstructed endoscopic image $I_{i \to j}$ and the actual endoscopic image $I_j$ as a loss.

The three-dimensional restoration unit 23 generates a three-dimensional model according to the structure of the large intestine at the time of the endoscopic examination by performing a three-dimensional restoration process on the basis of the depth obtained from the depth estimation unit 21 and the relative posture change of the endoscope camera obtained from the camera posture estimation unit 22. The three-dimensional restoration unit 23 outputs the three-dimensional model, the relative posture change of the endoscope camera, and the position of the endoscope camera to the unobserved area detection unit 25.

That is, the three-dimensional model generation means of the present example embodiment includes the depth estimation unit 21, the camera posture estimation unit 22, and the three-dimensional restoration unit 23.

The observation difficult area detection unit 24 detects the area corresponding to at least one of the areas in the endoscopic image where the brightness is equal to or higher than a predetermined value, where the blur level is equal to or larger than a predetermined value, and where the residue is present, as the observation difficult area, for example. That is, the observation difficult area detection unit 24 detects, based on the endoscopic images, the area in the luminal organ where the observation by the endoscope camera is estimated to be difficult, as the observation difficult area. Then, the observation difficult area detection unit 24 outputs the detection result of the observation difficult area to the unobserved area detection unit 25.

The unobserved area detection unit 25 detects the area that is missing in the three-dimensional model as the missing area on the basis of the relative posture change of the endoscope camera, the position of the endoscope camera, and the three-dimensional model. Specifically, for example, the unobserved area detection unit 25 detects the area in the the three-dimensional model corresponding to at least one of the area that is hidden by a shield such as folds and the area where imaging by the endoscope camera has not been performed continuously for a predetermined time or more, as the missing area. Also, for example, the unobserved area detection unit 25 detects the area in the three-dimensional model acquired from the three-dimensional restoration unit 23 during the last 5 seconds where the three-dimensional restoration has not been performed continuously for one second or more, as the missing area. Also, the unobserved area detection unit 25 performs processing for specifying an area corresponding to the detection result of the observation difficult area obtained from the observation difficult area detection unit 24 in the three-dimensional model generated by the three-dimensional restoration unit 23. Also, the unobserved area detection unit 25 detects the observation difficult area and the missing area in the three-dimensional model as the unobserved area. That is, the unobserved area detection unit 25 detects an area that is estimated to be not observed by the endoscope camera as the unobserved area on the basis of the three-dimensional model of the luminal organ in which the endoscope camera is present. Further, the unobserved area detection unit 25 can obtain the latest detection result in accordance with the observation history of the large intestine (intestinal tract) by the endoscope camera, as the detection result of the unobserved area in the three-dimensional model. Then, the unobserved area detection unit 25 outputs the relative posture change of the endoscope camera, the position of the endoscope camera, the three-dimensional model, and the detection result of the unobserved area to the display image generation unit 27.

The lesion candidate detection unit 26 detects a lesion candidate area that is an area estimated as a lesion candidate in the endoscopic image using a learned image recognition model or the like. More specifically, the lesion candidate detection unit 26 detects, for example, an area including a polyp as the lesion candidate area. That is, the lesion candidate detection unit 26 detects the lesion candidates area, which is estimated as the area of the lesion candidate, based on the endoscopic image obtained by imaging the interior of the luminal organ by the endoscope camera. Then, the lesion candidate detection unit 26 outputs the detection result of the lesion candidate area to the display image generation unit 27.

During the endoscopic examination, the display image generation unit 27 generates a display image on the basis of the endoscopic image, the relative posture change of the endoscope camera, the position of the endoscope camera, the detection result of the lesion candidate area, the three-dimensional model, and the detection result of the unobserved area in the three-dimensional model, and outputs the generated display image to the display device 2. Further, the display image generation unit 27 sets the display state of each information included in the display image (such as ON/OFF of display).

The display image may include at least one of information indicating the position of the unobserved area in the endoscopic image corresponding to the inside of the field of view of the endoscope camera and information indicating a direction of the unobserved area out of the endoscopic image corresponding to the outside of the field of view of the endoscope camera. Such information can be generated using, for example, the detection results of the unobserved areas accumulated during the period in which the endoscopic examination is being performed. That is, the display image generation unit 27 generates the display image including at least one of the information indicating the position of the unobserved area in the endoscopic image obtained by imaging the interior of the luminal organ by the endoscope camera and the information indicating the direction of the unobserved area outside the endoscopic image. Further, the display image generation unit 27 changes the display of information indicating the position of the unobserved area from ON to OFF, when it detects that the unobserved area existing in the endoscopic image has been imaged continuously more than a predetermined time.

Further, the display image may include at least one of information indicating the position of the lesion candidate area in the endoscopic image, information indicating the direction of the lesion candidate area outside the endoscopic image, and information indicating the latest detection result of the lesion candidate area. Such information can be generated, for example, using the detection results of the lesion candidate areas accumulated during the period in which the endoscopic examination is being performed.

According to the present example embodiment, in the case where multiple unobserved areas detected during the endoscopic examination exist outside the endoscopic image, information indicating the direction of one unobserved area, which is closest to the current position of the endoscope camera or which is the largest area, among the multiple unobserved areas may be included in the display image.

Further, according to the present example embodiment, for example, in the case where multiple lesion candidate areas detected during the endoscopic examination exist outside the endoscopic image, information indicating the direction of one lesion candidate area located closest to the current position of the endoscope camera among the multiple lesion candidate areas may be included in the display image.

Display Example

Figure 4:
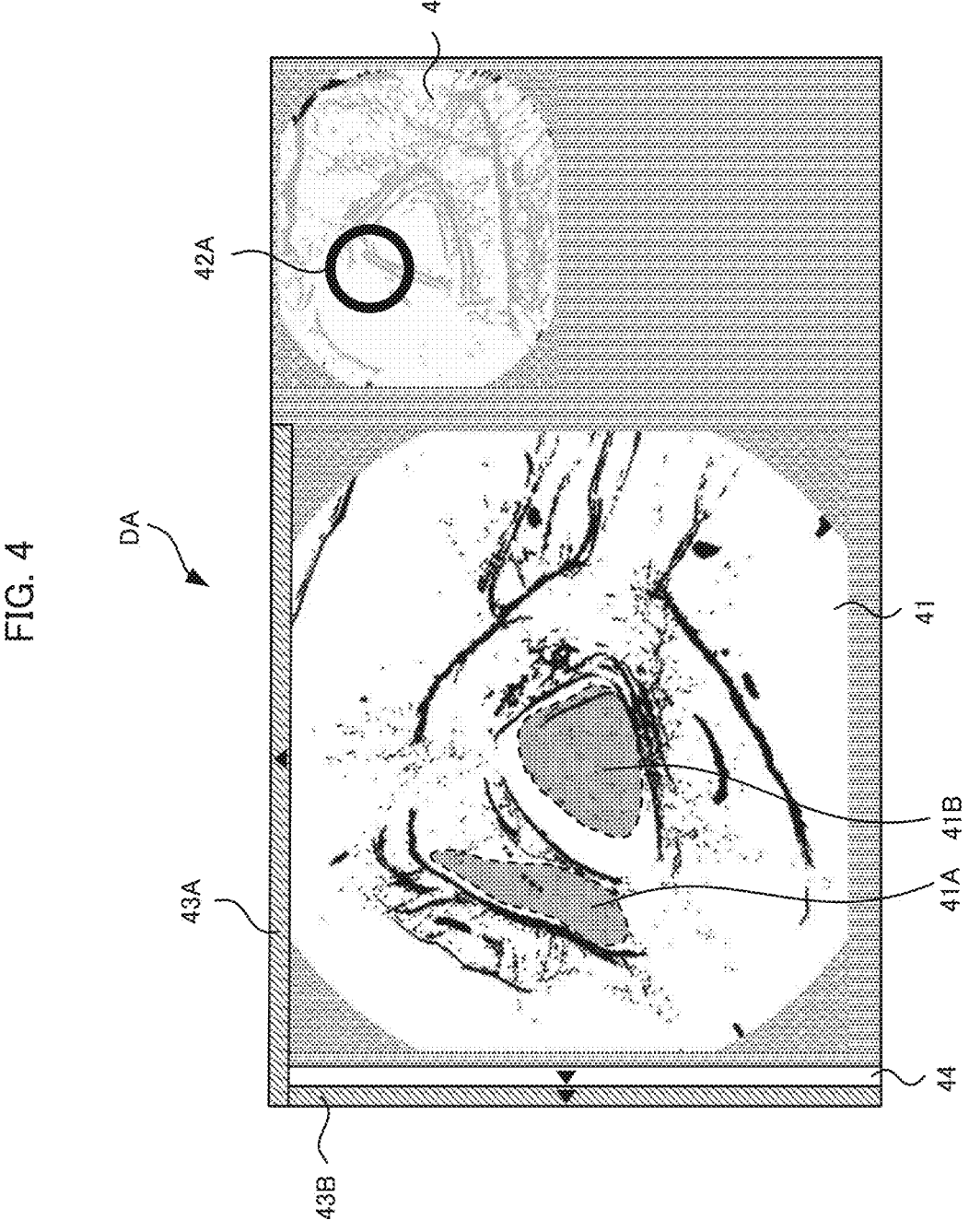
FIG. 4 is a diagram for explaining a specific example of a display image.

Subsequently, a specific example of a display image displayed on the display device 2 will be described. FIG. 4 is a diagram for explaining a specific example of a display image.

The display image DA of FIG. 4 is an image to be displayed on the display device 2 during the endoscopic examination. The display image DA includes an endoscopic image 41, a lesion candidate image 42, unobserved direction indicators 43A and 43B, and a lesion direction indicator 44.

The endoscopic image 41 is an image included in the endoscopic video Ic obtained during the endoscopic examination. The endoscopic image 41 includes a subject within the field of view at the current position of the endoscope camera and is updated according to the movement of the endoscope camera. In addition, the endoscopic image 41 includes unobserved area masks 41A and 41B which indicate the positions of the unobserved areas in the endoscopic image 41.

The unobserved area mask 41A is displayed in a display manner so as to cover the area in the endoscopic image 41 where the imaging by the endoscope camera has not been performed continuously for a predetermined time or more. For example, the unobserved area mask 41A is erased from the endoscopic image 41 when the imaging by the endoscope camera is performed continuously for the predetermined time or more.

The unobserved area mask 41B is displayed in a display manner to cover the area that is difficult to see due to insufficient brightness in the endoscopic image 41. For example, the unobserved area mask 41B is continuously displayed, when the brightness in the endoscopic image 41 is equal to or lower than a predetermined value, even if the imaging by the endoscope camera is performed continuously for a predetermined time or more. For example, the unobserved area mask 41B is erased from the endoscopic image 41 when imaging by the endoscope camera is performed continuously for the predetermined time or more, after it is detected that the brightness in the endoscopic image 41 becomes higher than the predetermined value.

The lesion candidate image 42 has a smaller size than the endoscopic image 41 and is located on the right side of the endoscopic image 41. The lesion candidate image 42 is an image generated by superimposing the lesion position information 42A on other endoscopic image acquired prior to the timing at which the endoscopic image 41 was acquired.

The lesion position information 42A is displayed as information indicating the latest detection result of the lesion candidate area. According to the display example of FIG. 4, the lesion position information 42A is displayed as a circular marker surrounding the periphery of the lesion candidate area.

The unobserved direction indicators 43A and 43B are displayed as the information indicative of the direction of the unobserved area existing outside the endoscopic image 41.

Here, according to the display example of FIG. 4, the unobserved direction indicator 43A having a mark indicating the upward direction is displayed at a position adjacent to the upper end of the endoscopic image 41, and the unobserved direction indicator 43B having a mark indicating the left direction is displayed at a position adjacent to the left end of the endoscopic image 41. That is, according to the unobserved direction indicators 43A and 43B of FIG. 4, it can be informed to the operator that the unobserved area outside the endoscopic image 41 exists in the upper left direction with respect to the current position of the endoscope camera.

In the present example embodiment, one of the unobserved direction indicators 43A and 43B may be displayed. Specifically, for example, if the unobserved direction indicator 43A is displayed but the unobserved direction indicator 43B is not displayed, the operator can be informed that the unobserved area outside the endoscopic image 41 is located in the upward direction with respect to the current position of the endoscope camera. Also, for example, if the unobserved direction indicator 43B is displayed but the unobserved direction indicator 43A is not displayed, the operator can be informed that the unobserved area outside the endoscopic image 41 is located in the left direction with respect to the current position of the endoscope camera.

In addition, in the present example embodiment, for example, an indicator similar to the unobserved indicators 43A and 43B may be further displayed at a position adjacent to the lower end of the endoscopic image 41 and a position adjacent to the right end of the endoscopic image 41. In such a case, the operator can be informed that the unobserved area outside the endoscopic image 41 is present in any of eight directions (upward, upward right, right, downward right, downward, downward left, left and upward left) with respect to the current position of the endoscope camera.

The lesion direction indicator 44 is displayed as information indicating the direction of the lesion candidate area outside the endoscopic image 41.

Here, according to the display example of FIG. 4, the lesion direction indicator 44 having a mark indicating the left direction is displayed at a position adjacent to the left end of the endoscopic image 41. That is, according to the lesion direction indicator 44 of FIG. 4, it can be informed to the operator that the lesion candidate area outside the endoscopic image 41 exists in the left direction with respect to the current position of the endoscope camera.

Incidentally, in the present example embodiment, for example, an indicator similar to the lesion direction indicator 44 may be displayed at a position adjacent to the upper end of the endoscopic image 41, a position adjacent to the lower end of the endoscopic image 41, and a position adjacent to the right end of the endoscopic image 41. In such a case, the operator can be informed that the lesion candidate area outside the endoscopic image 41 exists in any of eight directions (upward, upward right, right, downward right, downward, downward left, left, and upward left) with respect to the current position of the endoscope camera.

According to the display image DA of FIG. 4, during endoscopic examination, the position of the unobserved area in the endoscopic image 41, the direction of the unobserved area outside the endoscopic image 41, and the direction of the lesion candidate area outside the endoscopic image 41 can be displayed at the same time. Further, according to the display image DA of FIG. 4, the display of the unobserved area masks 41A and 41B are changed from ON to OFF according to the observation state during the endoscopic examination. Further, according to the display image DA of FIG. 4, the display of the indicators indicating the direction of the unobserved area outside the endoscopic image 41 can be set ON or OFF, and the display of the indicator indicating the direction of the lesion candidate area outside the endoscopic image 41 can be set ON or OFF, depending on the position and/or direction of the endoscope camera during the endoscopic examination.

Figure 5:
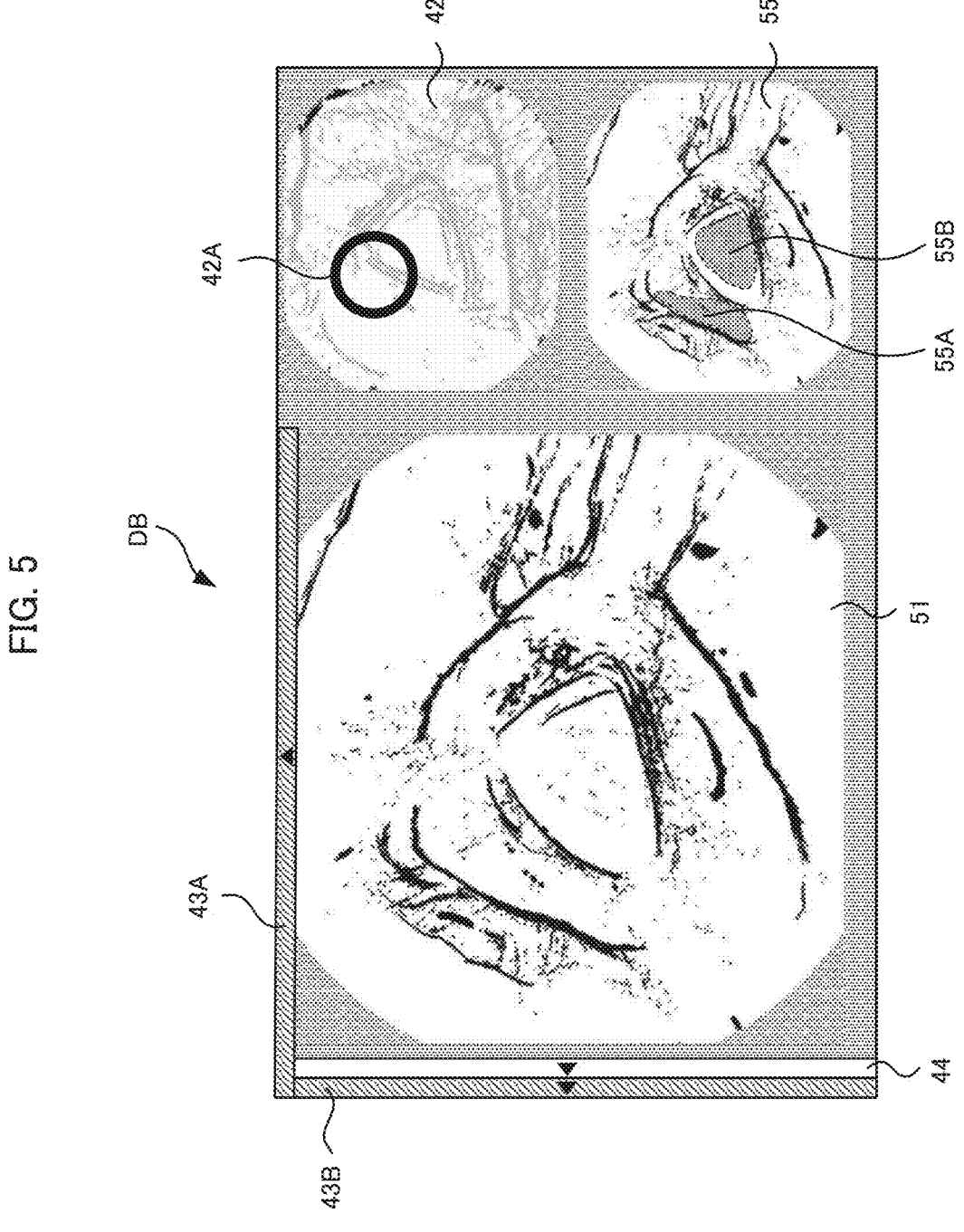
FIG. 5 is a diagram for explaining another specific example of the display image.

On the other hand, in the present example embodiment, instead of the display image DA shown in FIG. 4, the display image DB as shown in FIG. 5 may be displayed on the display device 2. FIG. 5 is a diagram for explaining another specific example of a display image. For the sake of simplicity, a specific description of the parts to which the configuration described above can be applied shall be omitted in the following description.

The display image DB of FIG. 5 is an image to be displayed on the display device 2 during the endoscopic examination. The displayed image DB includes an endoscopic image 51, a lesion candidate image 42, unobserved direction indicators 43A and 43B, a lesion direction indicator 44, and an unobserved area confirmation image 55.

The endoscopic image 51 corresponds to the image obtained by removing the unobserved area masks 41A and 41B from the endoscopic image 41.

The unobserved area confirmation image 55 corresponds to an image obtained by reducing the size of the endoscopic image 51 and adding information indicating the position of the unobserved area in the endoscopic image 51. The unobserved area confirmation image 55 is arranged on the right side of the endoscopic image 51 and the lower side of the lesion candidate image 42. The unobserved area confirmation image 55 is updated at the same time as the update of the endoscopic image 51. Further, the unobserved area confirmation image 55 includes unobserved area masks 55A and 55B which are information indicating the positions of the unobserved areas in the endoscopic image 51.

The unobserved area mask 55A is displayed in a display manner so as to cover the area in the endoscopic image 51 where the imaging by the endoscope camera has not been performed continuously for a predetermined time or more. For example, the unobserved area mask 55A is erased from the unobserved area confirmation image 55 when the imaging by the endoscope camera is performed continuously for the predetermined time or more.

The unobserved area mask 55B is displayed in a display manner to cover an area that is difficult to see due to insufficient brightness in the endoscopic image 51. For example, the unobserved area mask 55B is continuously displayed when the brightness in the endoscopic image 51 is equal to or lower than a predetermined value, even if the imaging by the endoscope camera is performed continuously for the predetermined time or more. For example, the unobserved area mask 55B is erased from the unobserved area confirmation image 55 when the imaging by the endoscope camera is performed continuously for the predetermined time or more after it is detected that the brightness in the endoscopic image 51 is higher than the predetermined value.

According to the display image DB of FIG. 5, the same information as the respective information included in the display image DA of FIG. 4 can be displayed while maintaining a state in which the whole area of the endoscopic image obtained during the endoscopic examination can be confirmed in detail. Further, according to the display image DB of FIG. 5, it is possible to change the display state of the respective information in the same manner as the display image DA of FIG. 4 (ON-OFF of the display).

[Processing Flow]

Figure 6:
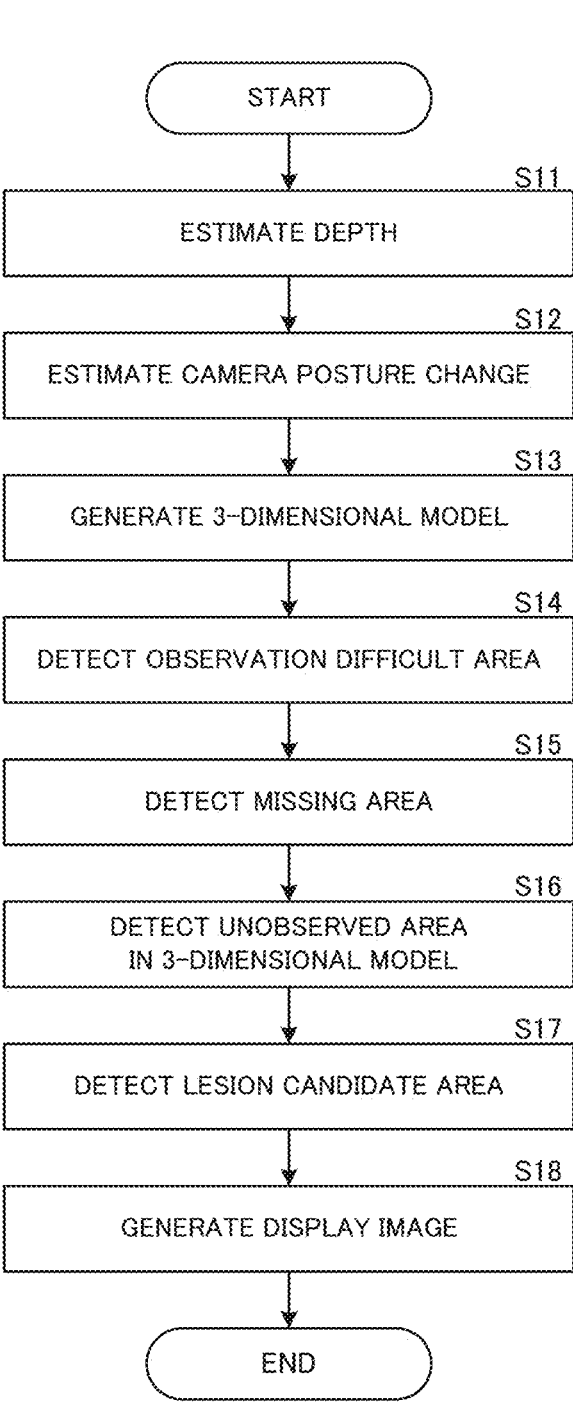
FIG. 6 is a flowchart illustrating an example of processing performed by the endoscopic examination support apparatus according to the first example embodiment.

Subsequently, a flow of processing performed in the endoscopic examination support apparatus according to the first example embodiment will be described. FIG. 6 is a flowchart illustrating an example of processing performed in the endoscopic examination support apparatus according to the first example embodiment.

First, the endoscopic examination support apparatus 1 estimates the depth from the endoscopic images obtained during the endoscopic examination (step S11).

Next, the endoscopic examination support apparatus 1 estimates the camera posture change from two endoscopic images successive in time obtained during the endoscopic examination (step S12).

Subsequently, the endoscopic examination support apparatus 1 generates a three-dimensional model according to the structure of intestinal tract of the large intestine at the time of the endoscopic examination by performing the three-dimensional restoration process on the basis of the depth obtained in step S11 and the camera posture change obtained in step S12 (step S13).

Subsequently, the endoscopic examination support apparatus 1 detects the observation difficult area based on the endoscopic images obtained during the endoscopic examination (step S14).

Subsequently, the endoscopic examination support apparatus 1 detects the missing area in the three-dimensional model generated in step S13 (step S15).

Subsequently, in the three-dimensional model generated in step S13, the endoscopic examination support apparatus 1 detects the area corresponding to the observation difficult area detected in step S14 and the area corresponding to the missing area detected in step S15, as the unobserved areas (step S16).

Subsequently, the endoscopic examination assisting device 1 detects the lesion candidate area based on the endoscopic images obtained during the endoscopic examination (step S17).

Subsequently, the endoscopic examination support apparatus 1 generates a display image on the basis of the detection result of the unobserved area obtained in step S16 and the detection result of the lesion candidate area obtained in step S17 (step S18). The display image includes at least one of information indicating the position of the unobserved area in the endoscopic image obtained during the endoscopic examination and information indicating the direction of the unobserved area outside the endoscopic image. In addition, the display image includes information indicating the direction of the lesion candidate area outside the endoscopic image. Then, the display image generated in step S18 is displayed on the display device 2.

In the present example embodiment, the process of step S12 may be executed prior to step S11, or the process of step S11 may be executed simultaneously with the process of step S12.

As described above, according to the present example embodiment, the display state of the information indicating the position of the unobserved area in the endoscopic image and the information indicating the direction of the unobserved area outside the endoscopic image can be changed according to the position and/or the orientation of the endoscope camera during the endoscopic examination. Further, as described above, according to the present example embodiment, for example, by continuously imaging the unobserved area in the endoscopic image for a predetermined time or more, the display of information indicating the position of the unobserved area can be changed from ON to OFF. Therefore, according to the present example embodiment, it is possible to reduce the burden imposed on the operator who performs the endoscopic examination. In addition, it can be used for support such as user's decision making.

Second Example Embodiment

Figure 7:
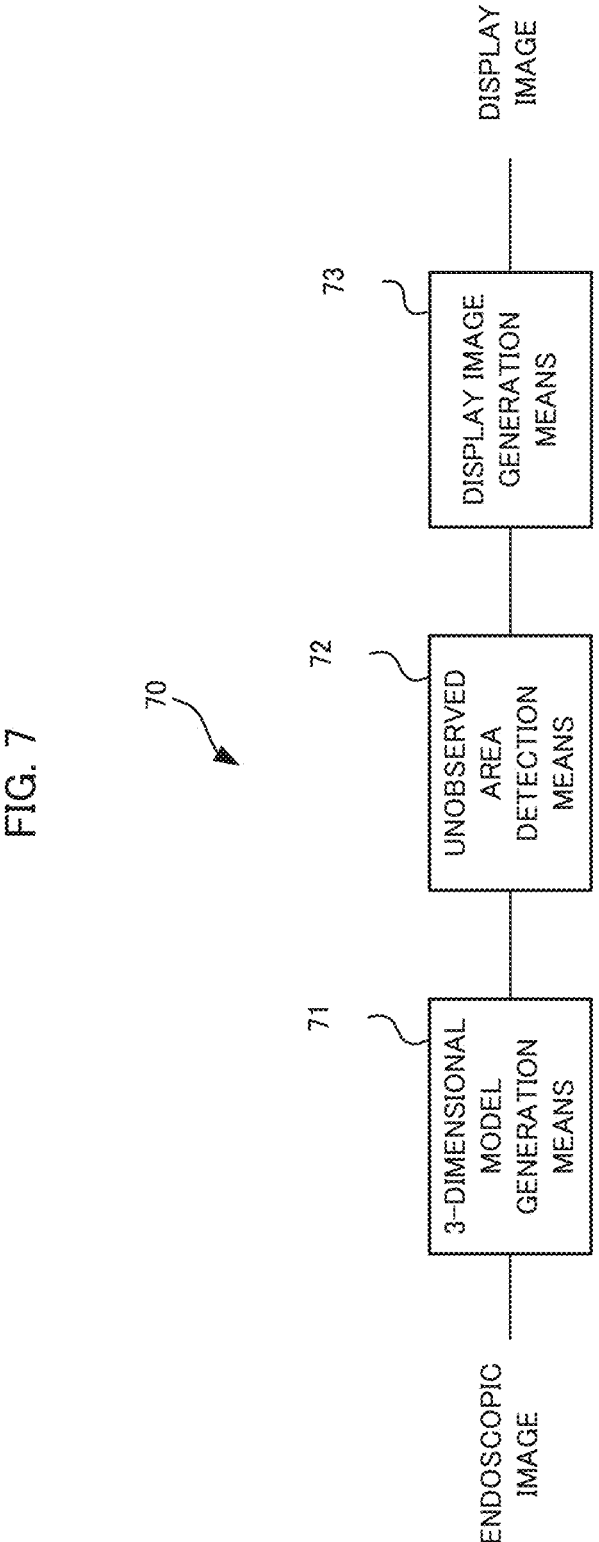
FIG. 7 is a block diagram showing a functional configuration of an endoscopic examination support apparatus according to a second example embodiment.

FIG. 7 is a block diagram illustrating a functional configuration of an endoscopic examination support apparatus according to a second example embodiment.

The endoscopic examination support apparatus 70 according to this example embodiment has the same hardware configuration as the endoscopic examination support apparatus 1. Further, the endoscopic examination support apparatus 70 includes a three-dimensional model generation means 71, an unobserved area detection means 72, and a display image generation means 73.

Figure 8:
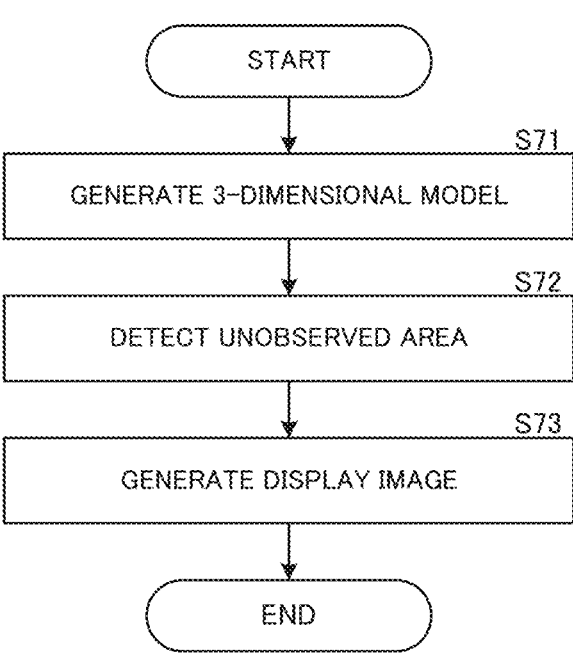
FIG. 8 is a flowchart illustrating an example of processing performed by the endoscopic examination support apparatus according to the second example embodiment.

FIG. 8 is a flowchart illustrating an example of processing performed in the endoscopic examination support apparatus according to the second example embodiment.

The three-dimensional model generation means 71 generates a three-dimensional model of a luminal organ in which an endoscope camera is placed, based on endoscopic images obtained by imaging an interior of the luminal organ with the endoscope camera (step S71).

The unobserved area detection means 72 detects an area estimated not to be observed by the endoscope camera, as an unobserved area, based on the three-dimensional model (step S72).

The display image generation means 73 generates a display image including at least one of information indicating a position of the unobserved area in the endoscopic image, and information indicating a direction of the unobserved area outside the endoscopic image (step S73).

According to this example embodiment, it is possible to reduce the burden imposed on the operator who performs the endoscopic examination.

A part or all of the example embodiments described above may also be described as the following supplementary notes, but not limited thereto.

Supplementary Note 1

An endoscopic examination support apparatus comprising:

a three-dimensional model generation means configured to generate a three-dimensional model of a luminal organ in which an endoscope camera is placed, based on endoscopic images obtained by imaging an interior of the luminal organ with the endoscope camera;

an unobserved area detection means configured to detect an area estimated not to be observed by the endoscope camera, as an unobserved area, based on the three-dimensional model; and a display image generation means configured to generate a display image including at least one of information indicating a position of the unobserved area in the endoscopic image, and information indicating a direction of the unobserved area outside the endoscopic image.

Supplementary Note 2

The endoscopic examination support apparatus according to Supplementary note 1, wherein the unobserved area detection means detects, as the unobserved area, at least one of an observation difficult area for which observation by the endoscope camera in the luminal organ is estimated to be difficult, and a missing area of the three-dimensional model.

Supplementary Note 3

The endoscopic examination support apparatus according to Supplementary note 2, wherein the observation difficult area corresponds to at least one of the area in the endoscopic image where brightness is equal to or lower than a predetermined value, the area where blurred amount is equal to or larger than a predetermined value, and the area where residue is present, and wherein the unobserved area detection means detects, as the unobserved area, an area corresponding to the observation difficult area in the three-dimensional model.

Supplementary Note 4

The endoscopic examination support apparatus according to Supplementary note 2, wherein the missing area is an area in the three-dimensional model corresponding to at least one of the area hidden by a shield in the luminal organ and the area for which imaging by the endoscope camera is not performed continuously for a predetermined time or more.

Supplementary Note 5

The endoscopic examination support apparatus according to Supplementary note 1, wherein, when detecting that the unobserved area in the endoscopic image has been imaged continuously for a predetermined time or more, the display image generation means changes the display of the information indicating the position of the unobserved area in the endoscopic image from ON to OFF.

Supplementary Note 6

The endoscopic examination support apparatus according to Supplementary note 1, further comprising a lesion candidate detection means configured to detect a lesion candidate area which is an area estimated to be a lesion candidate by a learned machine learning model based on the endoscopic image, wherein the display image generation means generates the display image including information indicating a direction of the lesion candidate area outside the endoscopic image.

Supplementary Note 7

The endoscopic examination support apparatus according to Supplementary note 6, wherein the display image generation means generates the display image including information indicating a latest detection result of the lesion candidate area.

Supplementary Note 8

An endoscopic examination support method comprising:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including at least one of information indicating a position of the unobserved area in the endoscopic image, and information indicating a direction of the unobserved area outside the endoscopic image.

Supplementary Note 9

A recording medium storing a program, the program causing a computer to execute:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including at least one of information indicating a position of the unobserved area in the endoscopic image, and information indicating a direction of the unobserved area outside the endoscopic image.

This application is based upon and claims the benefit of priority from the international application PCT/JP2022/029426 filed Aug. 1, 2022, and its entire disclosure is incorporated herein by reference.

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

DESCRIPTION OF SYMBOLS

1 Endoscopic examination support apparatus
2 Display device
3 Endoscope
11 Processor
12 Memory
13 Interface
21 Depth estimation unit
22 Camera posture estimation unit
23 Three-dimensional restoration unit
24 Observation difficult area detection unit
25 Unobserved area detection unit
26 Lesion candidate detection unit
27 Display image generation unit
100 Endoscopic examination system

The invention claimed is:

1. An endoscopic examination support apparatus comprising:

a memory configured to store instructions; and a processor configured to execute the instructions to:

generate a three-dimensional model of a luminal organ in which an endoscope camera is placed, based on endoscopic images obtained by imaging an interior of the luminal organ with the endoscope camera;

detect an area estimated not to be observed by the endoscope camera, as an unobserved area, based on the three-dimensional model; and generate a display image including an information indicative of a direction of an unobserved area existing outside the endoscopic image displayed at least one of positions adjacent to the upper and lower ends and the left and right ends of the endoscopic image, depending on the direction in which the unobserved area is located with respect to the current position of the endoscope camera, wherein the display image includes an unobserved area mask displayed in a display manner so as to cover the unobserved areas in the endoscopic image, and wherein the processor is further configured to execute the instructions to change the display of the unobserved area mask in the endoscopic image from ON to OFF, when detecting that the unobserved area in the endoscopic image has been imaged continuously for a predetermined time or more.

2. The endoscopic examination support apparatus according to claim 1, wherein an information indicative of a direction of un unobserved area existing outside the endoscopic image can be changed ON-OFF depending on the position and/or direction of the endoscope camera.

3. The endoscopic examination support apparatus according to claim 1, wherein the processor is further configured to execute the instructions to:

estimate a depth from endoscopic images obtained by imaging an interior of the luminal organ with the endoscope camera;

estimate a relative posture change of the endoscope camera from two endoscopic images successive in time; and generate a three-dimensional model of a luminal organ in which an endoscope camera is placed, by performing a three-dimensional restoration process on a basis of the depth and the relative posture change of the endoscope camera.

4. The endoscopic examination support apparatus according to claim 3, wherein the processor is further configured to execute the instructions to:

estimate the depth using an image recognition model which is a machine learning model learned in advance; and estimate the relative posture change of the endoscope camera using an image recognition model which is a machine learning model learned in advance.

5. The endoscopic examination support apparatus according to claim 1, wherein the processor is further configured to execute the instructions to detect, as the unobserved area, at least one of an observation difficult area for which observation by the endoscope camera in the luminal organ is estimated to be difficult, and a missing area of the three-dimensional model.

6. The endoscopic examination support apparatus according to claim 5, wherein the observation difficult area corresponds to at least one of the area in the endoscopic image where brightness is equal to or lower than a predetermined value, the area where blur level is equal to or larger than a predetermined value, and the area where residue is present, and wherein the processor is further configured to execute the instructions to detect, as the unobserved area, an area corresponding to the observation difficult area in the three-dimensional model.

7. The endoscopic examination support apparatus according to claim 5, wherein the missing area is an area in the three-dimensional model corresponding to at least one of the area hidden by a shield in the luminal organ and the area for which imaging by the endoscope camera is not performed continuously for a predetermined time or more.

8. The endoscopic examination support apparatus according to claim 1, wherein the processor is further configured to execute the instructions to:

detect a lesion candidate area which is an area estimated to be a lesion candidate by a learned machine learning model based on the endoscopic image; and generate the display image including information indicating a direction of the lesion candidate area outside.

9. The endoscopic examination support apparatus according to claim 8, wherein the processor is further configured to execute the instructions to generate the display image including information indicating a latest detection result of the lesion candidate area.

10. An endoscopic examination support method comprising:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including an information indicative of a direction of un unobserved area existing outside the endoscopic image displayed at least one of positions adjacent to the upper and lower ends and the left and right ends of the endoscopic image, depending on the direction in which the unobserved area is located with respect to the current position of the endoscope camera, wherein the display image includes an unobserved area mask displayed in a display manner so as to cover the unobserved areas in the endoscopic image, and wherein the display of the unobserved area mask in the endoscopic image is changed from ON to OFF, when detecting that the unobserved area in the endoscopic image has been imaged continuously for a predetermined time or more.

11. A non-transitory computer-readable recording medium storing a program, the program causing a computer to execute:

generating a three-dimensional model of a luminal organ in which an endoscope camera is placed, based on endoscopic images obtained by imaging an interior of the luminal organ with the endoscope camera;

detecting an area estimated not to be observed by the endoscope camera, as an unobserved area, based on the three-dimensional model; and generating a display image including an information indicative of a direction of un unobserved area existing outside the endoscopic image displayed at least one of positions adjacent to the upper and lower ends and the left and right ends of the endoscopic image, depending on the direction in which the unobserved area is located with respect to the current position of the endoscope camera, wherein the display image includes an unobserved area mask displayed in a display manner so as to cover the unobserved areas in the endoscopic image, and wherein the display of the unobserved area mask in the endoscopic image is changed from ON to OFF, when detecting that the unobserved area in the endoscopic image has been imaged continuously for a predetermined time or more.

* * * * *